United States Patent [19]

Abushanab et al.

[11] Patent Number: 5,760,208
[45] Date of Patent: Jun. 2, 1998

[54] PROCESS TO PREPARE PYRIMIDINE NUCLEOSIDES

[75] Inventors: Elie Abushanab, Peacedale, R.I.; Palle V.P. Pragnacharyulu, Bridgton, Mo.

[73] Assignee: The Board of Governors for Higher Education, State of Rhode Island and Providence Plantations, Providence, R.I.

[21] Appl. No.: 804,636

[22] Filed: Feb. 25, 1997

Related U.S. Application Data

[63] Continuation-in-part of Ser. No. 696,535, Aug. 14, 1996, abandoned.

[51] Int. Cl.⁶ .......................... C07H 1/00; C07H 19/073
[52] U.S. Cl. ........................... 536/55.3; 536/28.54
[58] Field of Search .................... 536/553, 28.54

[56] References Cited

PUBLICATIONS

Pragnacharulu et al. J. Org. Chem. 60:3096–3099, 1995.
Barvian et al. J. Org. Chem. 58:6151–6154, 1993.
Rao et al. J. Chem Soc. Commun. 1255,1256, 1994.
Sawai et al. Chem. Lett. 605–606, 1994.
Sawai et al. J. Chem. Soc. Chem. Commun. 1997–1998, 1994, No Month is Available.

*Primary Examiner*—Gary L Kunz
*Attorney, Agent, or Firm*—Samuels, Gauthier, Stevens & Reppert

[57] ABSTRACT

A process for the production of a compound of the formula:

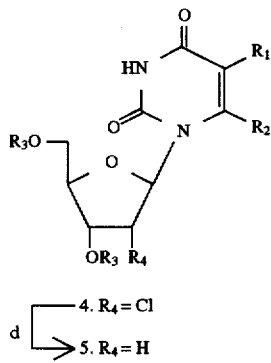

wherein $R_1$ is hydrogen, alkyl, $C_1$–$C_{16}$ substituted alkyl, aryl, substituted aryl, aralkyl, substituted aralkyls, alkenyl, substituted alkenyl, alkynyl, substituted alkynyl, cyano, carboxy, carboxy esters, carboxamido, or N-mono substituted and N,N-disubstituted carboxamido with alkyl, aralkyl or aryl groups; $R_2$ is hydrogen, alkyl $C_1$–$C_{16}$ substituted alkyl, aryl, substituted aryl, aralkyl, substituted aralkyls, alkenyl, substituted alkenyl, alkynyl or substituted alkynyl; $R_3$ is alkyl $C_2$–$C_6$, branched alkyl, aryl $C_2$–$C_6$ or substituted aryl and $R_4$ is halogen or H.

A condensation reaction is effected between compounds of the formulae:

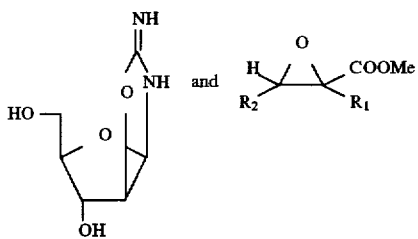

to form a novel compound of the formula:

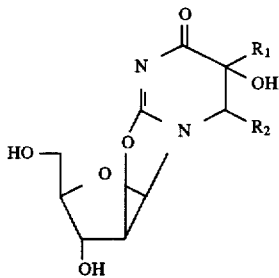

Compound (2) is acylated with a compound of the formula:

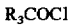

to form a novel compound of the formula:

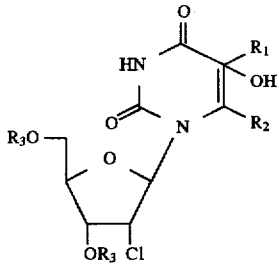

Compound (3) is mixed with pyridine and is reacted with thionyl chloride to form compound (4) and compound (4) is dehalogenated to form compound (5).

4 Claims, 1 Drawing Sheet

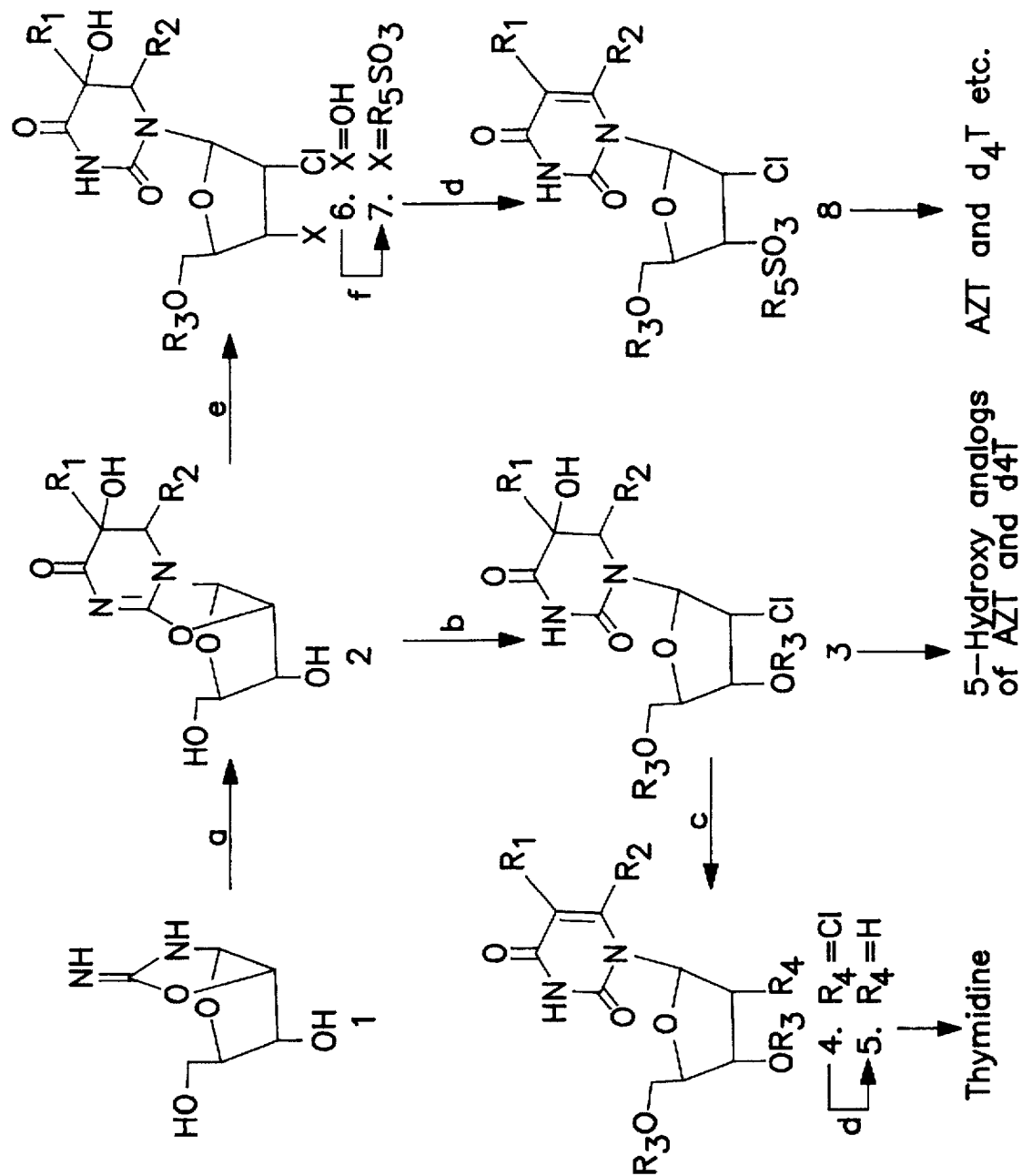

PROCESS TO PREPARE PYRIMIDINE NUCLEOSIDES

CROSS-REFERENCE TO RELATED APPLICATION(S)

This application is a continuation-in-part application of U.S. patent application Ser. No. 08/696,535 filed Aug. 14, 1996, now abandoned.

BACKGROUND AND BRIEF SUMMARY OF THE INVENTION

Pyrimidine nucleosides are important antiviral agents, increased attention has recently been focused on these compounds with the FDA approval of 3'-azido-2',3'-dideoxythymidine (AZT) stavudine (D$_4$T) as an effective treatment for Acquired Immunodeficiency Syndrome (AIDS). Since the synthesis of such agents utilizes the pyrimidine nucleoside β-thymidine as a starting material, new methods for the low-cost production of this and other synthetic intermediates are also becoming important. The present invention involves an expeditious route to the O$^2$,2'-anhyro-1-(β-arabinofuranosyl) 5-hydroxy 5,6 dihydro pyrimidine nucleosides, a class of compounds easily converted to the β-pyrimidine derivatives. Analogous syntheses of these anhydronucleosides is described in the following publications.

Japanese Kokai No. 81 49 398 laid open on May 2, 1981 refers to the synthesis of acylated arabinofuranosylcyclothymine compounds. The process of the Japanese Kokai requires that the iminoarabino(1 2:4.5) oxazoline acid addition salt be acylated.

In an article appearing in J. Mo. Biol., 1970, 47, 537 the authors describe the use of a readily available aminooxazoline carbohydrate derivative as a useful precursor to a variety of anhydronucleosides.

In the reference Kampe, K. D.; Justus Leibigs AnnChem., 1974, (4), 593–607 (ger), reactions of aminooxazolines with unsaturated esters are disclosed. European patent application 0 351 126 discloses a process for the formation of O$^2$,2'-anhydro-1-(β-D-arabinofuranosyl)thymine by reacting 2-amino-β-D-arabinofurano-oxazoline(s) with an alkyl 3-halo or alkoxy-methacrylate derivative.

In U.S. Pat. No. 5,077,403 discloses a process which starts with acrylates or acrylonitriles and related derivatives; compounds that are at a lower oxidation state than other substrates previously used for similar condensations This results in the formation of 5,6-dihydro pyrimidine nucleoside derivatives which are then oxidized to the required nucleosides in high to excellent yields.

Since the issuance of the '403 patent, the following articles have been published.

Pragnacharyulu, Palle V. P.; Vargeese, Chandra; McGregor, Michael; Abushanab, Elie, Diastereomeric 5,-6-Dihydrothymidines. Preparation, Stereochemical Assignments, and MnO$_2$ Oxidation Studies to Thymidines, Journal of Organic Chemistry, pp. 3096–3099, 60, 1995;

Rao, A. V. Rama; Gurjar, Mukund K.; Lalitha, Sista V. S., Discovery of a Novel Route to β-Thymidine: a Precursor for anti-AIDS Compounds, J. Chem. Soc., Chem. Commun., pp. 1255–1256, 1994;

Barvian, Mark R.; Greenberg, Marc M., Diastereoselective Synthesis of Hydroxylated Dihydrothymidines Resulting from Oxidative Street, J. Org. Chem., 58, 6151–6154, 1993;

Sawai, Hiroaki; Nakamura, Akiko; Sekiguchi, Sumie; Yomoto, Keisuke; Endoh, Masakazu; Ozaki, Hiroaki; Efficient Synthesis of New 5-Substituted Uracil Nucleosides Useful for Linker Arm Incorporation, J. Chem. Soc., Chem. Commun., pp. 1997–1998, 1994; and Sawai, Hiroaki; Hayashi, Hidekazu; Sekiguchi, Sumie, Facile Synthesis of 5-Substituted Arabinofuranosyluracil Derivatives, Chemistry Letters, pp. 605–606, 1994.

Broadly, the present invention is directed to a process for the production of pyrimidine nucleoside compounds of the formula:

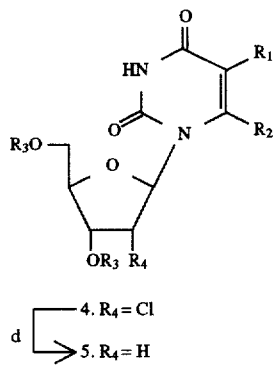

and the enantiomers thereof, wherein R$_1$, is hydrogen, alkyl C$_1$–C$_{16}$ substituted alkyl, aryl, substituted aryl, aralkyl, substituted aralkyls, alkenyl, substituted alkenyl, alkynyl, substituted alkynyl, cyano, carboxy, carboxy esters, carboxamido, N-mono substituted and N,N-disubstituted carboxamido with alkyl, aralkyl and aryl groups; R$_2$ is hydrogen, alkyl C$_1$–C$_{16}$ substituted alkyl, aryl, substituted aryl, aralkyl, substituted aralkyls, alkenyl, substituted alkenyl, alkynyl, substituted alkynyl; R$_3$ is alkyl C$_2$–C$_6$, branched alkyl, aryl C$_2$–C$_6$, substituted aryl and R$_4$ is halogen or H.

A Michael type condensation reaction is effected on a compound of the formula:

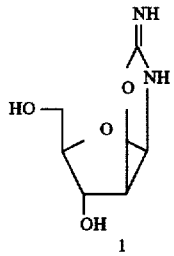

with a compound of the formula

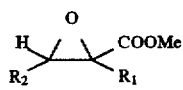

to form a novel compound of the formula

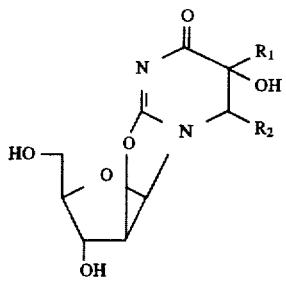
(2)

Compound (2) is acylated with a compound of the formula:

$R_3COCl$ to form novel compounds (3) and (6) depending upon the duration of the reaction.

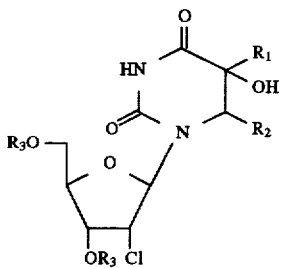
(3)

In the preferred embodiment, compound (3) is mixed with pyridine and is reacted with thionyl chloride to form compound (4) where $R_4=Cl$.

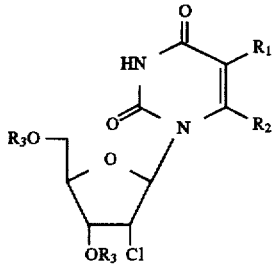
(4)

Compound (4) is dihalogenated to form compound (5).

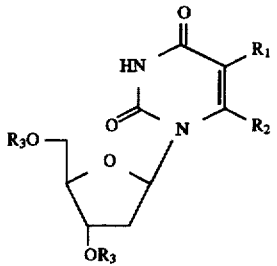
(5)

Compound (5) can be hydrolyzed by any well known process to form thymidine.

In an alternative embodiment of the invention, compound (6) is mixed with pyridine and is reacted with alkyl or aryl sulfonyl halide to form a novel compound of the formula (7).

Compound (7) is then mixed with pyridine and thionyl chloride to form a compound of the formula (8).

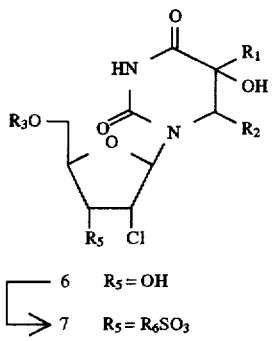
(7)

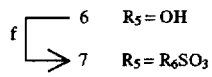

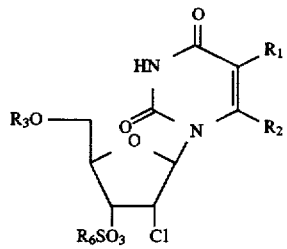
(8)

where $R_6$ is alkyl $C_2-C_6$, branched alkyl, aryl $C_2-C_6$, substituted aryl Compound (8) can be converted to either AZT or $d_4t$ as described in the chemical literature, B. C. Chen. et al., Tetrahedron letters 36, 7957-7960 (1995); B. C. Chen. et al., Tetrahedron letters 36, 7961-7964 (1995).

The present disclosure embodies several inventive embodiments. One embodiment of the invention is a process for the production of compounds (4) and (5); another embodiment of the invention comprises the compound (2) and the method for the production of compound (2); another embodiment comprises compound (3) and the method for the production of compound (3) and the conversion of compound (3) into 5 hydroxy 5,6 dihydro pyrimidines, e.g. AZT, $d_4t$; another embodiment comprises novel compounds (6) and (7) and the processes for the production of compounds (6) and (7); and lastly, another embodiment of the invention comprises a process for the production of compound (8).

BRIEF DESCRIPTION OF THE DRAWINGS

The FIGURE illustrates reaction schemes of the invention.

DESCRIPTION OF THE PREFERRED EMBODIMENT(S)

Presently, there are several methods to produce prymidine nucleosides, however these methods are limited in their utility either because they cannot form 5 substituted prymidine derivatives directly or involve long synthetic routes resulting in increased cost and reduced yields. The synthetic route disclosed in the '403 patent, although advantageous in view of the then prior art synthesis, still resulted in high cost primarily because of the oxidizing agent found most efficacious in the process, namely DDQ.

In the present invention the condensation reaction between the starting oxazoline (1) is effected with a compound which is itself oxidized resulting in a new composition of matter, namely compound (2). One aspect of the invention embodies compound (2) and the method of making compound (6). Compound (2) is further reacted with pivaloyl chloride to form a new composition of matter, namely compound (3). Another aspect of the invention embodies compound (3) and the method of making compound (3). With the process of the invention the desired pyrimidine is produced efficiently and in high yields.

The first step of the process of the present invention comprises the condensation of an oxazoline derivative of formula (1) with a glycidate ester or glycidonitrile of formula (1a) to yield derivatives of formula (2). This process is preferably carried out at a temperature of about 50° C. to about 150° C., preferably at 80° C. to 100° C., in the presence of reaction-inert solvent. Preferred solvents are dimethyl acetamide, dimethyl formamide and other organic solvents such as $C_1$–$C_4$ alkanols, preferably methanol, dimethyl sulfoxide, acetone etc. can also be used. Water may also be used. Although preferred embodiment employs equimolar amounts of compounds (1) and glycidate ester (1a), an excess of either reagent may be used.

In the reaction between compounds (1) and the glycidate ester (1a), the pressure is not critical. Generally the reaction is conducted at a pressure of from about 0.5 to about 2.0 atmospheres, preferably at ambient pressure, (i.e. about one atmosphere).

The second step of the process comprises the selective acylation of (2) with concomitant opening of the anhydro bond by the halide ion at the 2'-position. While prolonged reaction times (24 h) lead to the di-acylated derivative (3), shortened reaction times (3 h) give the novel mono-acylated derivative (6). The reaction is preferably carried out in acetonitrile from about 50° C. to about 150° C., preferably at 80° C. to 100° C. Other solvents such as THF, dimethyl formamide, dimethyl acetamide can also be used.

The final step of the process involves dehydration of compounds of the formula (3) and (7) to the corresponding pyrimidine nucleosides. Thus, (3) and (7) upon treatment with thionyl chloride in pyridine lead to compounds of the formula (4) and (8) respectively. Other dehydrating agents such as trifluoroacetic anhydride, phosphorous pentoxide etc. can also be used. Preferred temperatures for this reaction is –40° C. to about 50° C., preferably 0–5° C. Other solvents such as trialkyl amines can also be used.

Three major advantages of this process over those of the prior art are low cost of the starting materials and the efficiency of the process, no $\alpha$ or $\beta$ mixtures in the final product, which permits a high yield of the desired compound and formation of new composition of matter (2) which provides access to novel and new 5-hydroxylated analogs of drugs in clinical use such as AZT and $d_4T$.

Chemistry
Experimental:

2,2'-Anhydro-1-β-D-arabino-furanosyl-5-hydroxy-5, 6-dihydrothymine (2)

A mixture of aminooxazoline derivative 1 (87 mg, 0.5 mmol) and methyl 2-methyl glycidate (0.23 mg, 2 mmol) in toluene (5 mL) was heated at 90° C. for 48 h. The solvent was removed under reduced pressure and the residue was chromatographed on silica gel eluting first with EtoAc to remove non-polar impurities followed by 15% EtoAc to give 2 as 1:1 diastereomeric mixture (100 mg, 78%): $^1$HNMR (300 MHz, $D_2O$) δ1.29 (s, 3H), 3.48–3.68 (m, 4H), 4.25–4.29 (m, 1H), 4.53–4.55 (m, 1H), 5.30 (d, J=5.7 Hz, 1H), 6.01 (d, J=5.7 Hz), 6.06 (d, J=5.7 Hz), (1H).

Anal. Calcd for $C_{10}H_{14}N_2O_6$: C, 46.51; H, 5.46; N, 10.84. Found: C, 46.67; H, 5.87; N, 10.63.

1-(3',5'-Di-O-Pivaloyl-2'-chloro-2'-deoxy-β-D-ribofuranosyl)-5-hydroxy-5,6-dihydro-thymine (3)

Compound 2 (200 mg, 0.75 mmol) and pivaloyl chloride (1.5 mL) were dissolved in AcCN (15 mL) and the mixture was refluxed for 24 h. AcCN was removed under reduced pressure and the residue was partitioned between $CH_2Cl_2$ and aq. $NaHCO_3$, water and brine, respectively. Removal of $CH_2Cl_2$ gave, after silica gel column chromatography (20% <<50% EtoAc/hexanes), the title compound 3 as diastereomeric mixture (190 mg, 57%): $^1$H NMR (300 MHz, $CDCl_3$) δ1.24 (s, 9H), 1.26 (s, 9H), 1.52 (s) 1.66 (s) (3H), 3.36 (AB quartet centre, $\Delta u_{AB}$=61.2 Hz, $J_{AB}$=12.8 Hz, 2H), 4.16–4.49 (m, 5H, 1H $D_2O$ exchangeable), 5.24 (dd, J=5.9, 2.7 Hz, 1H), 6.09 (d, J=7.3 Hz), 6.1 (d, J=8.1 Hz) (1H), 8.68 (s) 8.84 (s) (1H, $D_2O$ exchangeable).

1-(3', 5'-di-O-Pivaloyl-2'-chloro-2'-chloro-2'-deoxy-β-D-ribofuranosyl)thymine (4)

Compound 3 (30 mg, 0.069 mmol) was taken in pyridine (2 mL) and the mixture was cooled in an ice bath under argon. Thionyl chloride (0.1 mL, 1.36 mmol) was added dropwise and the mixture was stirred at the same temperature for 3 h. $CH_2Cl_2$ (30 mL) was added to the reaction mixture and the organic layer was washed with dil. HCl, water and brine. Removal of $CH_2Cl_2$ gave a residue which was purified by column chromatography (20% EtOAc/hexanes) to give 4 (16 mg, 60% ). $^1$H NMR (90 MHz, $CDCl_3$) 1.3 (s, 18H), 1.95 (s, 3H), 4.0–4.6 (m, 4H), 5.1–5.3 (m, 1H), 6.1 (d, J=7.0 HZ, 1H), 7.25 (s, 1H), 8.9 (bs, 1H, $D_2O$ exchangeable).

1-(3',5'-Di-O-pivaloyl-2'-deoxy-β-D-ribofuranosyl)-thymine (5)

Tributyltin hydride (100 mg, 0.36 mmol), azabisisobutyronitrile (5 mg) and compound 5 (43 mg, 0.1 mmol) were dissolved in anhydrous toluene (5 mL) and refluxed for 3 h. The residue obtained after concentrating the reaction mixture was purified by column chromatography over silica gel using EtOAc/hexanes (1:1) as eluent to provide 5 (35 mg, 85%) as a gum. $^1$H NMR (90 MHz, $CDCl_3$) 1.3 (s, 18H), 1.7–2.6 (m, 5H), 3.9–4.5 (m, 3H), 5.0–5.2 (m, 1H), 6.1–6.3 (dt, 1H), 7.3 (s, 1H), 9.3 (bs, 1H).

1-(5'-O-Pivaloyl-2'-chloro-2'-deoxy-β-D-ribofuranosyl)-5-hydroxy-5,6- dihydro-thymine (6)

Compound 2 (258 mg, 1 mmol) and pivaloyl chloride (1.0 mL) were dissolved in AcCN (15 mL) and the mixture was refluxed for 24 h. AcCN was removed under reduced pressure and the residue was partitioned between $CH_2Cl_2$ and aq. $NaHCO_3$, water and brine, respectively. Removal of $CH_2Cl_2$ gave, after silica gel column chromatography (20% <<50% EtoAc/hexanes), the title compound 6 as diastereomeric mixture (200 mg, 53%): $^1$H NMR (90 MHz, $CDCl_3$) 1.2 (s, 9H), 1.9 (s, 3H), 3.0 (bs, 2H, $D_2O$ exchangeable), 3.4 (AB quartet centre, $\Delta u_{AB}$=21 Hz, $J_{AB}$ =23 Hz, 2H), 4.0–4.5 (m, 5H) 6.0–6.2 (m, 1H), 8.8 (bs, 1H, $D_2O$ exchangeable).

1-(5'-O-Pivaloyl-3'-p-toluenesulphonyl-2'-chloro-2'-deoxy-β-D-ribofuranosyl)-5-hydroxy-5,6-dihydro-thymine (7)

Compound 6 (40 mg, 0.1 mmol) was taken in pyridine (2 mL) and the mixture was cooled in an ice bath under argon. P-toluenesulphonyl chloride (100 mg) was added and the mixture was stirred at the room temperature for 3 h. $CH_2Cl_2$ (30 mL) was added to the reaction mixture and the organic layer was washed with dil. HCl, water and brine. Removal of $CH_2Cl_2$ gave a residue which was purified by column chromatography (20% EtOAc/hexanes) to give 7 (40 mg, 71%). $^1$H NMR (90 MHz, $CDCl_3$) 1.3 (s, 9H), 1.5 (s, 3H), 2.8 (bs, 1H, D$_2$O exchangeable), 3.1–3.4 (m, 2H), 4.1–4.5 (m, 4H), 4.9–5.1 (m, 1H), 5.9 d, J=7.0 Hz, 1H) 7.4 (d, J=7.0 Hz, 2H), 7.9 (d, J=7.0 Hz, 2H), 8.4 (bs, 1H, D$_2$O exchangeable).

The preferred embodiment of the invention has been described with reference to a starting compound of D-arabinose to synthesize β-D-nucleosides and particularly 2' deoxy nucleosides. As would be understood by one skilled in the art, the enantiomer of D-arabinose, namely L-arabinose can be used as a starting compound. The L-arabinose can be used with the same reactants and/or reagents and under the same reaction conditions, described for the preferred embodiment, to produce α-L-nucleosides. The reaction scheme to produce α-L-nucleosides is set forth below.

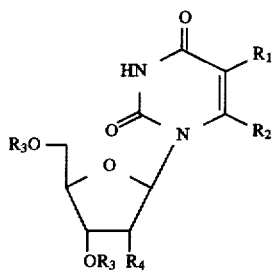

(4) (5)

and enantiomers thereof where R$_1$ is hydrogen, alkyl, C$_1$–C$_{16}$ substituted alkyl, aryl, substituted aryl, aralkyl, substituted aralkyls, alkenyl, substituted alkenyl,

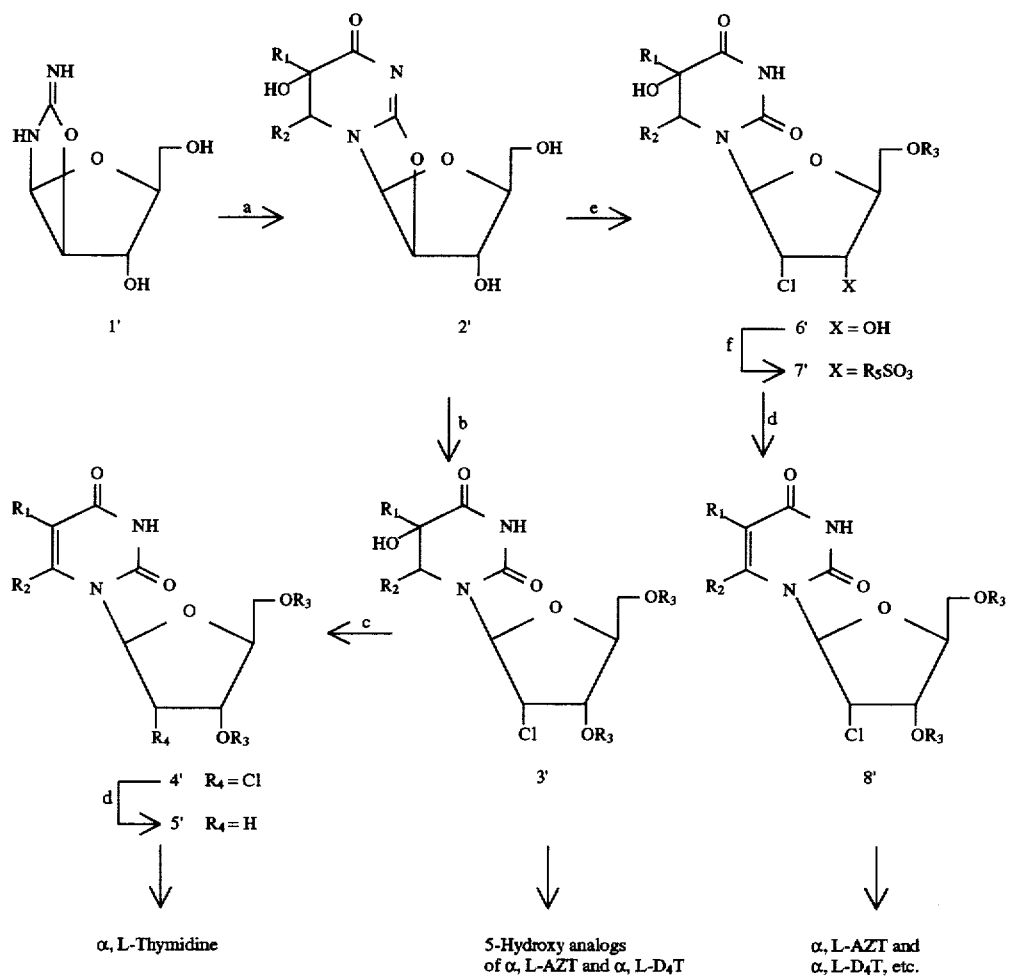

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described our invention, what we now claim is:

1. A process for the production of a compound of the formula:

alkynyl, substituted alkynyl, cyano, carboxy, carboxy esters, carboxamido or N-mono substituted and N,N-disubstituted carboxamido with alkyl, aralkyl or aryl groups;

where R$_2$ is hydrogen, alkyl, C$_1$–C$_{16}$ substituted alkyl, aryl, substituted aryl, aralkyl, substituted aralkyls, alkenyl, substituted alkenyl, alkynyl or substituted alkynyl;

where R$_3$ is alkyl C$_2$–C$_6$, branched alkyl, aryl C$_2$–C$_6$ or substituted aryl;

where R$_4$ is halogen or H;

effecting a condensation reaction on a compound of the formula:

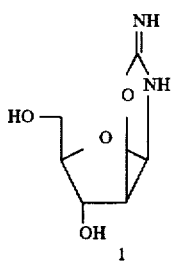

(1)

with a compound of the formula:

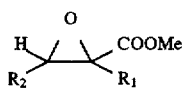

(1a)

to form a compound of the formula:

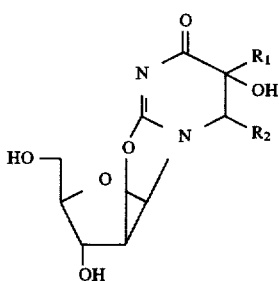

(2)

acylating compound (2) with a compound of the formula:

R₃COCl to form compound of the formula:

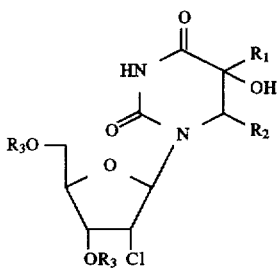

(3)

reacting compound (3) with thionyl chloride to form a compound of the formula:

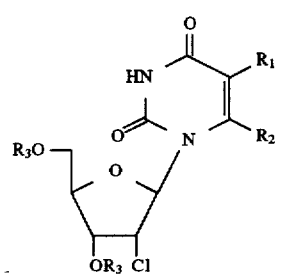

(4)

2. The process of claim 1 which further comprises: dehalogenating compound (4) to form a compound of the formula:

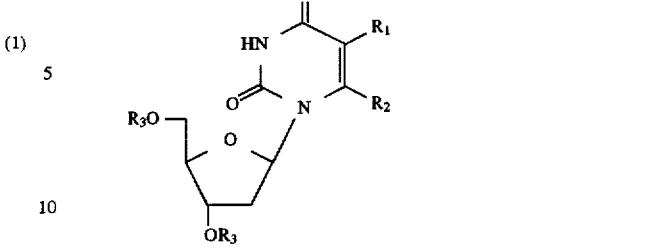

(5)

3. A compound of the formula:

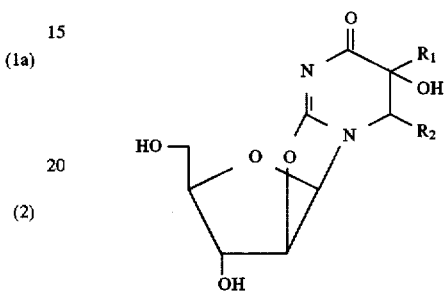

where $R_1$ is hydrogen, alkyl, $C_1$–$C_{16}$ substituted alkyl, aryl, substituted aryl, aralkyl, substituted aralkyls, alkenyl, substituted alkenyl, alkynyl, substituted alkynyl, cyano, carboxy, carboxy esters, carboxamido or N-mono substituted and N,N-disubstituted carboxamido with alkyl, aralkyl or aryl groups; and where $R_2$ is hydrogen, alkyl $C_1$–$C_{16}$ substituted alkyl, aryl, substituted aryl, aralkyl, substituted aralkyls, alkenyl, substituted alkenyl, alkynyl, substituted alkynyl.

4. A compound of the formula:

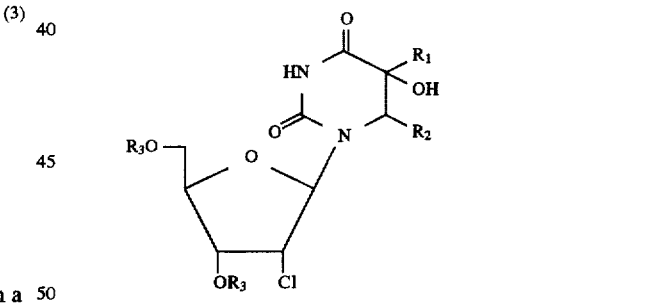

where $R_1$ is hydrogen, alkyl, $C_1$–$C_{16}$ substituted alkyl, aryl, substituted aryl, aralkyl, substituted aralkyls, alkenyl, substituted alkenyl, alkynyl, substituted alkynyl, cyano, carboxy, carboxy esters, carboxamido or N-mono substituted and N,N-disubstituted carboxamido with alkyl, aralkyl or aryl groups;

where $R_2$ is hydrogen, alkyl $C_1$–$C_{16}$ substituted alkyl, aryl, substituted aryl, aralkyl, substituted aralkyls, alkenyl, substituted alkenyl, alkynyl or substituted alkynyl; and where R3 is alkyl $C_2$–$C_6$, branched alkyl, aryl $C_2$–$C_6$ or substituted aryl.

* * * * *